United States Patent [19]
Tiraby et al.

[11] Patent Number: 5,856,153
[45] Date of Patent: Jan. 5, 1999

[54] SUICIDE GENES AND NEW ASSOCIATIONS OF PYRIMIDINE NUCLEOBASE AND NUCLEOSIDE ANALOGS WITH NEW SUICIDE GENES FOR GENE THERAPY OF ACQUIRED DISEASES

[75] Inventors: Gérard Tiraby, Toulouse; Jean-Paul Reynes, Escalquens; Michéle Tiraby, Toulouse; Christophe Cazaux, Plaisance du Touch; Daniel Drocourt, Saint Orens, all of France

[73] Assignee: Cayla, Toulouse, France

[21] Appl. No.: 343,923

[22] Filed: Nov. 17, 1994

[51] Int. Cl.$^6$ .................................................. C12N 15/85
[52] U.S. Cl. .................................... 435/172.3; 435/320.1; 435/172.1; 435/325; 435/353; 435/354; 435/363; 435/366; 435/69.7; 435/194; 435/227; 514/44; 424/93.2; 935/14; 935/32; 935/62; 935/66
[58] Field of Search ............................. 435/320.1, 172.3, 435/172.1, 240.2, 69.7, 194, 227, 325, 353, 354, 363, 364; 514/44; 536/23.2, 23.4

[56] References Cited

U.S. PATENT DOCUMENTS 5,021,344  6/1991  Armau et al. ......................... 435/172.3
5,118,620  6/1992  Armau et al. ......................... 435/172.3

FOREIGN PATENT DOCUMENTS 0 402 108  6/1990  European Pat. Off. .
WO 93/01281  6/1992  WIPO .

OTHER PUBLICATIONS

Rennie et al. (eds.) 1996 Scientific American 275(3): 126–132.
Orkin et al., 7 Dec. 1995 "Report and Recommendations of the Panel to Assess the NIH Investments in Research on Gene Therapy".
Calos 1996 TIG 12(11): 463–466.
Andersen et al. *Eur J Biochem* 204, 51–6 (1992).
Austin E.A. & Huber B.E. *J. Bacteriol* 175, 3685–5 (1993).
Baer et al. *Nature* 310, 207–211 (1984).
Binkley J.P. & Kuempel P.L. *J. Bacteriol* 168, 1457–8 (1986).
Black M.E. & Hruby D.E. *Mol. Microbiol* 5, 373–9 (1991).
Bockamp et al. *Gene* 101, 9–14 (1991).
Carter et al. *J. Bacteriol* 175, 3812–22 (1993).
Copeland, *J Biol Chem* 267, 21459–64 (1992).
Cornet et al. *J. Bacteriol* 176, 3188–95 1994.
Danielsen et al. *Mol Microbiol* 6, 1335–44 (1992).
Dong et al. *J. Biol Chem* 268, 11758–65 (1993).
Drocourt et al. *Nucleid Acids Res* 18, 4009 (1990).
Furman et al. *Proc Natl Acad Sci USA* 83, 8333–7 (1986).
Green et al. *J Bacteriol* 174, 5317–23 (1992).
Hama et al. *Gene* 105, 31–6 (1991).
Huber et al., *Cancer Res.* 53, 4619–26 (1993).
Jund R. & Lacroute F. *Journal of Bacteriology* 102, 607–615 (1970).
Kern et al. *Gene* 88, 149–57 (1990).
Kilstrup et al., *J. Bacteriol* 171, 2124–7 (1989).
Koechlin et al., *Biochem Parmacol.* 15, 435–446 (1966).
Kohara et al. *Cell* 50, 495–508 (1987).
Kornberg A. & Baker T. *In DNA replication* Freeman, W.M. and Company, New York, 53–100 (1992).
Littler et al. *EMBO J.5*, 1959–1966 (1986).
Mori et al. *Intervirology* 29, 301–310 (1988).
Mulkins M.A. & Heidelberger C. *Cancer Res.* 42, 965–73 (1982).
Mullen et al., *Cancer Res.* 54, 1503–6 (1994).
Mullen et al., *Proc. Natl. Acad. Sci. USA* 89, 33–37 (1992).
Munch–Petersen A. & Mygind B. *In. Metabolism of nucleotides, nucleosides and nucleobases in microorganism* (1983), 95–148, (Neuhard J., "Utilization of Performed Pyrimidine Gases and Nucleosides").
Natalini et al. *J. Biol. Chem.* 254, 1558–1563 (1979).
Plagemann et al., *Biochim Biophys. Acta* 947, 405–43 (1988).
Rawlings M. & Cronan J. J. *J. Biol. Chem.* 267, 5751–4 (1992).
Robertson G. & Whalley J.M. *Nucl. Acids Res.* 16, 11303–11317 (1988).
Ross, C. *Plant Physiol.* 40, 65–73 (1965).
Schwartz et al., *Biochem Pharmacol* 34, 3585–9 (1985).
Thomas K.R. & Capecchi M.R. *Cell* 51, 503–12 (1987).

Primary Examiner—Christopher S. F. Low
Attorney, Agent, or Firm—Larson & Taylor

[57] ABSTRACT

The present invention relates to two groups of suicide hybrid genes in which genes from one group specifically activate the pyrimidine nucleobase analog 5-fluorocytosine and genes from the other group activate the pyrimidine nucleoside analog azidothymidine to derivatives toxic for mammalian cells. The present invention further relates to methods for the selective killing of transfected tumor cells or immune cells using a single suicide hybrid gene or the combination of two suicide hybrid genes selected for a complementarity in their antimetabolic action. The present invention also relates to eukaryotic vectors comprising two expression suicide gene units, the first permitting the sensitization of tumor cells to 5-fluorocytosine and the second permitting the sensitization of HIV-infected cells to Azidothymidine in a synergistic fashion.

39 Claims, 8 Drawing Sheets

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTACCATGGT GTCGAATAAC GCTTTACAAA C                                      31

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTCCTAGGCG TTTGTAATCG ATGCCTTCTG GCTG                                 34

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTCATGCATC AAGATCGTGG AAGTCAAACA CCCA                                 34

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTGGTCGACA AGCTTATTTC GTACCAAAGA TTTTGTCACC                            40

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTAGGGATCT CAGGCCTTAA TGGCGTATGC A 31

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCTAGAGTCC GGAATTACCG CAT 23

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTACCATGGT GACAGGGGGA ATGCCAAGCA A 31

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCCCTAGGGC CTCACCAATA TCTTCAAACC AATCCTG 37

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TGGATGCATG AACCCGTTAT TCTTTTTGGC TTCT 34

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCGAGGTCGA CTTTAAACAC AGTAGTATCT GTCACCAAA 39

( 2 ) INFORMATION FOR SEQ ID NO:11:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

ATTTCGAATT CCCTCCCTGG AGGACAAACG TGT 33

( 2 ) INFORMATION FOR SEQ ID NO:12:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:12:

CCACCGGTAC CATCTCATGC GTCCAACTCC TTC 33

( 2 ) INFORMATION FOR SEQ ID NO:13:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

AGGACCATGG CCAGAAGTAA GTATATCGTC ATTGAGGGG 39

( 2 ) INFORMATION FOR SEQ ID NO:14:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:14:

TGCACGGACC GTTACGCGTC CAACTCCTTC ACCCAGTGG 39

( 2 ) INFORMATION FOR SEQ ID NO:15:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:15:

GTACCATGGC ACAGCTATAT TTCTACTAT 29

( 2 ) INFORMATION FOR SEQ ID NO:16:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear (i i) MOLECULE TYPE: DNA (genomic)

(x i) SEQUENCE DESCRIPTION: SEQ ID NO:16:

CTGGATCCCT AGGTCGTGGC GATGCCTTTC CTGAATAGCC 40

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

CCATATGCAT GGCTATTGAA CGTACTTTTT CCATCATCAA A 41

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

TGTGTCGACT TAACGGGTGC GCGGGCACAC TTCGCC 36

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

AGGACCATGG CCAGAAGTAA GTATATCGTC ATTGAGGGG 39

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

GACATGCATC CAGGTCCCTG GTCCAACTCC ACCCAGTGGG TC 42

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:21:

-continued

```
GTACCATGGC ATCAACGGAT AAAACCGATG TAAAAATG                                      3 8
```

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CGCCCTAGGG AAGTGTTGTC CTGAAC                                                   2 6
```

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
GGGAGCGCTG GATTTCCAGG AAAG                                                     2 4
```

( 2 ) INFORMATION FOR SEQ ID NO:24:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
AAGCCTAGGT CCCGATTTCC CCTCTC                                                   2 6
```

SUICIDE GENES AND NEW ASSOCIATIONS OF PYRIMIDINE NUCLEOBASE AND NUCLEOSIDE ANALOGS WITH NEW SUICIDE GENES FOR GENE THERAPY OF ACQUIRED DISEASES

BACKGROUND OF THE INVENTION

The present invention relates to molecular therapies for cancer and HIV infections in which tumor cells or immune cells are stably transduced with a variety of genes introduced by high efficiency delivery systems, such as retroviral and adenoviral vectors.

One strategy for the treatment of localized disease is to render targeted cells sensitive to normally nontoxic chemotherapeutic agents using so-called "suicide genes" such as the herpes simplex virus thymidine kinase (HSV-tk) gene, the related varicella zoster TK gene or the bacterial xanthine/guanine phosphoribosyltransferase gpt gene. HSV-tk, for example, converts the nontoxic guanosine analogue ganciclovir into a phosphorylated compound that acts as a chain terminator in DNA synthesis, selectively killing dividing cells.

The codA gene of *Escherichia coli* encoding cytosine deaminase (hereinafter referred to as CDase) represents another potential suicide gene to be used for the selective elimination of unwanted human cells. Cytosine deaminase is the first enzyme of the only metabolic pathway by which exogeneous cytosine or endogeneous cytosine from pyrimidine nucleotide breakdown is utilized by way of hydrolytic deamination to uracil and ammonia. Cytosine deaminases have been found in prokaryotes and lower eukaryotes but appear to be absent in higher eukaryotes, both in mammals as well as in plants [Koechlin et al., *Biochem Parmacol.* 15, 435–446 (1966)] [Ross, C. *Plant Physiol.* 40, 65–73 (1965)]. Cytosine deaminase also deaminates the innocuous fluorocytosine (hereinafter referred to as FC) into fluorouracil (hereinafter referred to as FU), a highly toxic compound when efficiently converted to 5-fluoro-UMP. Cells lacking cytosine deaminase activity either as a consequence of a mutational inactivation as illustrated by codA and fcyl (genes coding for cytosine deaminase) mutants of *Escherichia. coli* and *Saccharomyces cerevisiae* respectively, or because they are naturally deficient for this enzyme, as are mammalian and plant cells, are resistant to 5-fluorocytosine [Kilstrup et al., J. Bacteriol 171, 2124–7 (1989)] [Jund R. & Lacroute F. *Journal of Bacteriology* 102, 607–615 (1970)]. This property provides the basis for the use of the *E.coli* coda gene as a suicide or a negative selection gene in a number of recently reported experiments with mammalian and plant cells [Huber et al., *Cancer Res* 53, 4619–26 (1993); WO 93/01281; Mullen et al., *Cancer Res* 54, 1503–6 (1994)] where transformed cells were shown to have acquired cytosine deaminase activity and to be sensitive to treatment with 5-fluorocytosine.

In the patent application WO 93/01281, Mullen and Blaese described a negative selection system comprising a modified bacterial gene for cytosine deaminase that has the ability to produce a toxic antimetabolite from FC in eukaryotic cells. In addition, Mullen and Blaese claimed a double negative selection based on a modified cytosine deaminase gene and the herpes thymidine kinase gene in a selection involving 5-fluorocytosine and ganciclovir an acyclic nucleoside analog of guanosine where triphosphate derivatives of ganciclovir compete with dGTP. However, it should be noted that a large majority of tumour cells are not sensitive to such a method of therapy.

The differential sensitivity to FC between parent cells and cells transfected by a cytosine deaminase gene varies greatly according to cell lines. Almost no sensitivity to fluorocytosine was observed in murine melanoma B16 clones transfected by a codA bearing vector and retained for high expression of cytosine deaminase activity (as illustrated in example 8 hereafter). The poor fluorocytosine sensitivity of cultured cells expressing high CDase activity, a situation encountered with many tumors, as reported by J. D. Harris in an oral communication at the 1994 Cold Spring Harbor Laboratory meeting on gene therapy, could be accounted for by at least two potential mechanisms.

One is related to the transport of cytosine. All natural nucleobases and their fluorinated analogs are hydrophilic and diffuse through the plasma membrane only very slowly. Their efficient permeation is dependent on special transport proteins. Fluorocytosine is taken up in *E.coli* by a cytosine specific permease encoded by codB. The crucial role of an active cytosine transport system in determining fluorocytosine sensitivity in this bacteria was demonstrated with mutants deleted for the codb gene. The normal situation appears to be the opposite in mammals. Although mammalian cells possess a uracil transport system, cytosine is not actively transported in various cell lines or in human erythrocytes, where entry seems to be entirely by passive diffusion [Plagemann et al., *Biochim Biophys Acta* 947, 405–43 (1988)].

The other mechanism is based on the existence and relative importance of anabolic and catabolic pathways that modulate fluorouracil concentration. In microorganisms, endogenous uracil is directly converted to UMP by uracil phosphoribosyltransferase (UPRTase) and may also be converted to UMP and dUMP through the concerted action of uridine phosphorylase and uridine kinase [Munch-Petersen A. & Mygind B. In. Metabolism of nucleotides, nucleosides and nucleobases in microorganisms (1983)].

However, this two-step route operates only if either of the substrates for uridine phosphorylase, i.e. ribose-1-phosphate or desoxyribose 1-phosphate, and uracil are present at high intracellular concentrations. In animal cells, uracil and fluorouracil are metabolized in two steps to UMP and F-UMP via the uridine intermediate [Mulkins M. A. & Heidelberger C. Cancer Res 42, 965–73 (1982); Schwartz et al., *Biochem Pharmacol* 34, 3585–9 (1985)] in absence of uridine phosphoribosyl transferase activity [Kornberg A. & Baker T. In DNA replication Freeman, W. M. and Company, New York, 53–100 (1992)]. In addition, a proportion of uracil and fluorouracil are catabolized to the atoxic dihydrouracil and dihydrofluorouracil respectively.

Therefore, the toxicity of FC on cells expressing an introduced cytosine deaminase gene depends on the amount of the formed FU which is converted to 5-fluoro-UMP and, through the de novo pyrimidine pathway, to 5-fluoro-dUMP, an irreversible inhibitor of thymidylate synthase and hence of DNA synthesis by deprivation of dTTP [Kornberg A. & Baker T. In DNA replication Freeman, W. M. and Company, New York, 53–100 (1992)].

Another drug whose operation concerns the pyrimidine metabolic pathway, is Azidothymidine, for the treatment of human immuno deficiency virus (HIV)infection.

AZT is one of the primary chemotherapeutic agents used in the treatement of HIV infection. AZT readily enters cells and is converted to the nucleoside phosphates AZT-MP, AZT-DP and AZT-TP by the sequential action of thymidine kinase, thymidylate kinase and nucleoside diphosphokinase. AZT is rapidly converted to AZT-MP by thymidine kinase but the resulting AZT-MP accumulates since it is a very poor substrate for human thymidylate kinase. The concentration of AZT-MP is typically >50 fold higher than that of AZT-TP in human cell lines [Furman et al. *Proc Natl Acad Sci USA* 83, 8333–7 (1986)]. Although AZT-TP is an inefficient substrate for cellular DNA polymerases, AZT-MP is incorporated into DNA [Copeland, J Biol Chem 267,21459–64 (1992)].

SUMMARY OF THE INVENTION

The present invention relates to a group of suicide genes consisting of modified bacterial and fungal CDase genes fused with modified bacterial and fungal UPRTase genes, coding for a two-domain enzyme with both CDase and UPRTase activities, that have the property of producing a toxic antimetabolite from FC in those eukaryotic cells which are not sensitive to the FC metabolite produced by a single cytosine deaminase gene product. The invention also concerns a second group of new suicide genes which sensitize mammalian cells to Azidothymidine (AZT).

The invention further concerns eukaryotic vectors containing the two groups of suicide genes or either group alone, and a method of in situ treatment of cancer and of HIV infection by introduction of the said vectors into patients.

DETAILED DESCRIPTION OF THE INVENTION

This invention applies to situations where the mammalian cells transfected by a cytosine deaminase gene alone are not sensitive to FC as is the case with many tumors.

The Applicant company proposes the use of a modified gene coding for a single protein with both cytosine deaminase and UPRTase activities in tumor cells poorly sensitive to FC when transfected by a cytosine deaminase gene alone. The rationale is based on the expectation that in the case of two fusion proteins, FU would be more rapidly and efficiently converted to 5-fluoro-UMP. This would in turn generate an increase of the flux of FC entering cells particularly in tumor cells deprived of an active FC transport. Example 8 illustrates the dramatic enhancement of the killing effect following a FC treatment observed on murine melanoma B16 cells transfected, according to the invention; with a codA::upp (cytosine deaminase and which phosphoribosyl transferase) hybrid gene as compared with B16 cells transfected with a codA gene alone. These new suicide genes, resulting from the translational fusion between a cytosine deaminase gene and a UPRTase gene are to be used preferably in any situation where the targeted cells must be eliminated or the growth of targeted cells must be controlled.

It has been found that the order of the fusion UPRTase::CDase makes little, if any, difference in the specific activity of the enzyme compared to the fusion CDase::UPRTase enzyme. The *E.coli* codA::upp hybrid gene appears to be as efficient as the *S.cerevisiae* fcy1::fur1 hybrid gene. The smaller fcyl::upp gene could be preferred with delivery vectors such as retroviral, AAV or adenoviral vectors where the space for inserting genes is limited in size. The bifunctional genes encoding CDase and UPRTase activities constitute the first group of the new suicide genes of this invention.

The invention also concerns a second group of new suicide genes which sensitize mammalian cells to Azidothymidine (AZT) and/or pyrimidine nucleoside analogs such as dideoxythymidine, trifluoromethylthymidine, ethyldeoxyuridine, bromovinyldeoxyuridine or bromovinylarabinouracil.

A gene coding for a thymidylate kinase with a good affinity for AZT-MP would sensitize mammalian cells to AZT by providing more AZT triphosphates for incorporation into elongating DNA, thus causing chain termination and cell death. The AZT anabolizing enzymes of the bacteria *Escherichia coli*, which is highly sensitive to this drug, are good candidates to fullfil this requirement. The *E.coli* thymidylate kinase tmk gene alone, or fused to the *E.coli* thymidine kinase tdk gene or the *E.coli* nucleoside phosphokinase ndk gene, dramatically enhances the killing effect of AZT on the murine melanoma B16 cells. These new suicide genes may be used preferably in any situation where the targeted cells must be eliminated or the growth of targeted cells must be controlled.

The TK gene from a human herpes simplex virus codes for an enzyme with both thymidine kinase and thymidylate kinase activities. AZT is a poor substrate for the TK-HSV1 although the enzyme can phosphorylate a wide range of pyrimidine and purine nucleosides analogs. In the search for a thymidylate kinase enzyme of viral origin, able to phosphorylate AZT-MP, the Applicant company has discovered that the TK gene product from the Epstein-Barr virus substantially converts AZT-MP to AZT-DP. Therefore, the TK-EBV gene is a good candidate as a suicide gene to render AZT resistant mammalian cells sensitive to this drug. Another gene of great interest is the thymidylate kinase encoding tmk gene from *Escherichia coli*. In the search for a microorganism which would be naturally sensitive to low concentration of AZT added in the growth medium indicating an efficient AZT metabolism, the Applicant company has found that strains derived from *E.coli* K12 were the most sensitive of the several thousand bacterial and fungal strains tested. The *E.coli* tmk gene was isolated by gene cloning and modified, after the nucleotide sequence had been determined, in such a way that an active gene fusion could be made with other AZT-metabolizing genes susceptible to potentiate its action. The fusion of the tmk gene with the thymidine kinase encoding tdk gene or the nucleoside diphosphokinase encoding ndk gene, both from *E.coli*, are two examples of new suicide hybrid genes able to efficiently phosphorylate AZT. The bifunctional genes encoding thymidylate kinase and another activity of the pyrimidine de novo or salvage pathway constitute the second group of the new suicide genes of this invention.

In a preferred embodiment of the invention, which renders the new hybrid genes more convenient for DNA transfer experiments, the bifunctional genes from the two groups may be fused in the same reading frame as the small bacterial Sh ble gene, thus rendering mammalian cells resistant to an antibiotic of the phleomycin family (Armau et al, U.S. Pat. Nos. 5021344 and 5118620). Several of the phleomycin and zeocin selectable gene constructs with a negative phenotype are depicted in FIGS. 2A–2C.

It is worth noting in the context of this invention that genes possessing multiple functions are not anomalous cases in higher eukaryotes. For example the first three activities in animal cells of the de novo pyrimidine pathway which are coded by three unlinked genes in *E.coli*, are specified by a single gene resulting from the fusion of three distinct ancestral genes.

The invention further relates to the association of fluorocytosine and AZT for the combined chemotherapy of tumors by expression of two suicide genes, selected for complementarity in their modes of action and expressed in a eukaryotic vector.

The Applicant company has found that the depletion of dTTP by FC, activated by a suicide gene from the first group, would allow more AZT or one of the other pyrimidine nucleoside analogs, activated by a suicide gene from the second group, to be incorporated into DNA. As a consequence, tumor cells transformed by two suicide genes, one from the first group and the other from the second group, should be highly sensitive to the killing effect of a simultaneous treatement with FC and AZT or one of the other pyrimidine nucleoside analogs.

The antimetabolite AZT-TP competes with the natural nucleotide dTTP, although with a low efficiency, for incorporation into the DNA by the cellular polymerases. The higher the concentration ratio of AZT-TP/dTTP, the greater is the amount of AZT-TP that is incorporated into DNA. The blockage of the de novo synthesis of dTTP without interference regarding the formation of AZT-TP would change this ratio, leading to greater incorporation of the thymidine analog into DNA strands, thus terminating DNA elongation. Fluorocytosine, activated by cytosine deaminase or cytosine deaminase associated with UPRTase, is metabolized to the end product FdUMP which acts as a suicide inhibitor of thymidylate synthase, a key enzyme in the biosynthetic pathway of dTTP. The association of fluorocytosine and AZT in treating cells expressing two suicide genes to activate the two prodrugs acts synergistically to kill the cells. This mechanism is illustrated in FIG. 1.

The nucleotide dTTP is an essential metabolite, finely regulated in all cells. A severe depletion of dTTP by inhibitors or mutations induces the thymineless death of cells, possibly by induction of an endonuclease responsible for DNA double stranded breaks. The use of FC, activated by a gene coding for CDase and UPRTase activities, is intended to kill targeted cells by thymidine death due to dTTP starvation. Thymidine relieves the toxic effect of FC by furnishing dTTP after bypassing the thymidylate synthase blockage through the pyrimidine salvage pathway (see FIG. 1). The use of thymidine or deoxyuridine analogs in conjunction with FC for treating cells expressing two activator suicide genes has the opposite effect. The incorporation of triphosphate analogs into DNA by the replication and repair processes is facilitated by lack of the competing dTTP, leading to a more pronounced killing effect.

Accordingly, the invention encompasses a eukaryotic vector comprising two expression suicide gene units, the first permitting the sensitization of tumor cells to 5-fluorocytosine and the second permitting the sensitization of mammalian cells or HIV-infected cells to Azidothymidine in a synergistic fashion.

In a preferred embodiment, the eukaryotic vector comprises a first expression suicide gene unit comprising a hybrid gene, formed by the fusion of two bacterial genes or by the fusion of two fungal genes, said hybrid gene coding for a single protein having both cytosine deaminase and uracil phosphoribosyl transferase activities.

More preferably, the bacterial genes are the codA gene encoding cytosine deaminase and the upp gene encoding uracil phosphoribosyl transferase from *Escherichia coli* and the fungal genes are the fcyl gene encoding cytosine deaminase and the furl gene encoding uracil phosphoribosyl transferase from *Saccharomyces cerevisiae*.

The second expression suicide gene unit of the invention comprises a hybrid gene formed by the fusion of the tmk gene and a tdk encoding thymidine kinase gene from *Escherichia coli*, said hybrid gene coding for a single protein with both thymidine kinase and thymidylate kinase activities. Another candidate for the second expression suicide gene unit according to the invention is a hybrid gene formed by the fusion of a modified tmk gene from *Escherichia coli* and a ndk encoding nucleoside diphosphokinase from *Escherichia coli* and coding for a single protein having both thymidylate kinase and thymidine diphosphokinase activities, preferably with a further fusion with a Sh ble gene. The second expression suicide gene unit according to the invention may also comprise a modified tk gene from human Varicella-Zoster virus encoding thymidine kinase and thymidylate kinase activities, said modified gene having zeocin resistance or a similar gene from human Epstein-Barr virus.

A further object of the present invention relates to a method for in situ treatment of a tumor, comprising the steps of characterizing a tumor as one that is insensitive to pharmacologically acceptable doses of 5-fluorocytosine when expressing a transfected cytosine deaminase gene, transforming cells of said tumor in situ with a eukaryotic expression vector carrying a hybrid gene encoding cytosine deaminase and URPTase activities, then treating said tumor with pharmacologically acceptable doses of 5-fluorocytosine (FU).

Yet another concern of the present invention is a method for in situ treatment of a tumor, comprising the steps of transforming cells of said tumor in situ with a eukaryotic vector expressing a gene having thymidine kinase activities and thereafter treating said tumor with pharmacologically acceptable doses of azidothymidine (AZT).

The invention also concerns a method of therapy for human immunodeficiency virus (HIV) infection in a patient comprising the steps of inserting a eukaryotic vector carrying a gene encoding CDase and UPRTase activities, driven by a promoter or enhancer element from the HIV genome into the genome of hematopoietic cells in vitro reintroducing the transfected hematopoietic cells into said patient, and then treating said patient with FC in pharmacologically acceptable doses that will selectively kill HIV infected cells which integrate said eukaryotic vector.

The invention further concerns a method of therapy for human immunodeficiency virus (HIV) infection in a patient comprising the steps of inserting a eukaryotic vector carrying a gene encoding thymidine kinase type activities, driven by a promoter or enhancer element from the HIV genome into the genome of hematopoietic cells in vitro reintroducing the transfected hematopoietic cells into said patient, and then treating said patient with AZT in pharmacologically acceptable doses that will selectively kill HIV infected cells which integrate said eukaryotic vector.

The invention also concerns a method for in situ treatment of a tumor, comprising the steps of transforming cells of said tumor in situ with a eukaryotic vector expressing two suicide genes one coding for CDase and UPTRase activities and the other coding for thymidine kinase activities, and thereafter treating said tumor simultaneously or in alternance with low doses of FC and AZT.

The invention finally concerns a method for in situ treatment of a tumor, comprising the steps of transforming cells of said tumor in situ with a eukaryotic vector expressing two suicide genes one coding for CDase and UPRTase activities and the other coding for thymidine kinase activities and thereafter treating said tumor simultaneously or in alternance with low doses of FC and a pyrimidine nucleoside analog such as dideoxythymidine, trifluoromethylthymidine, ethyldeoxyuridine, bromovinyldeoxyuridine, bromovinyl-arabinouracil.

The steps catalyzed by products of the main new suicide genes of the second group described in the invention, in the anabolism of some non toxic thymidine and uridine nucleoside analogs are also indicated. The analogs are converted by the new suicide gene products to their triphosphate derivatives which are incorporated into DNA resulting in DNA inhibition.

Figure 1:
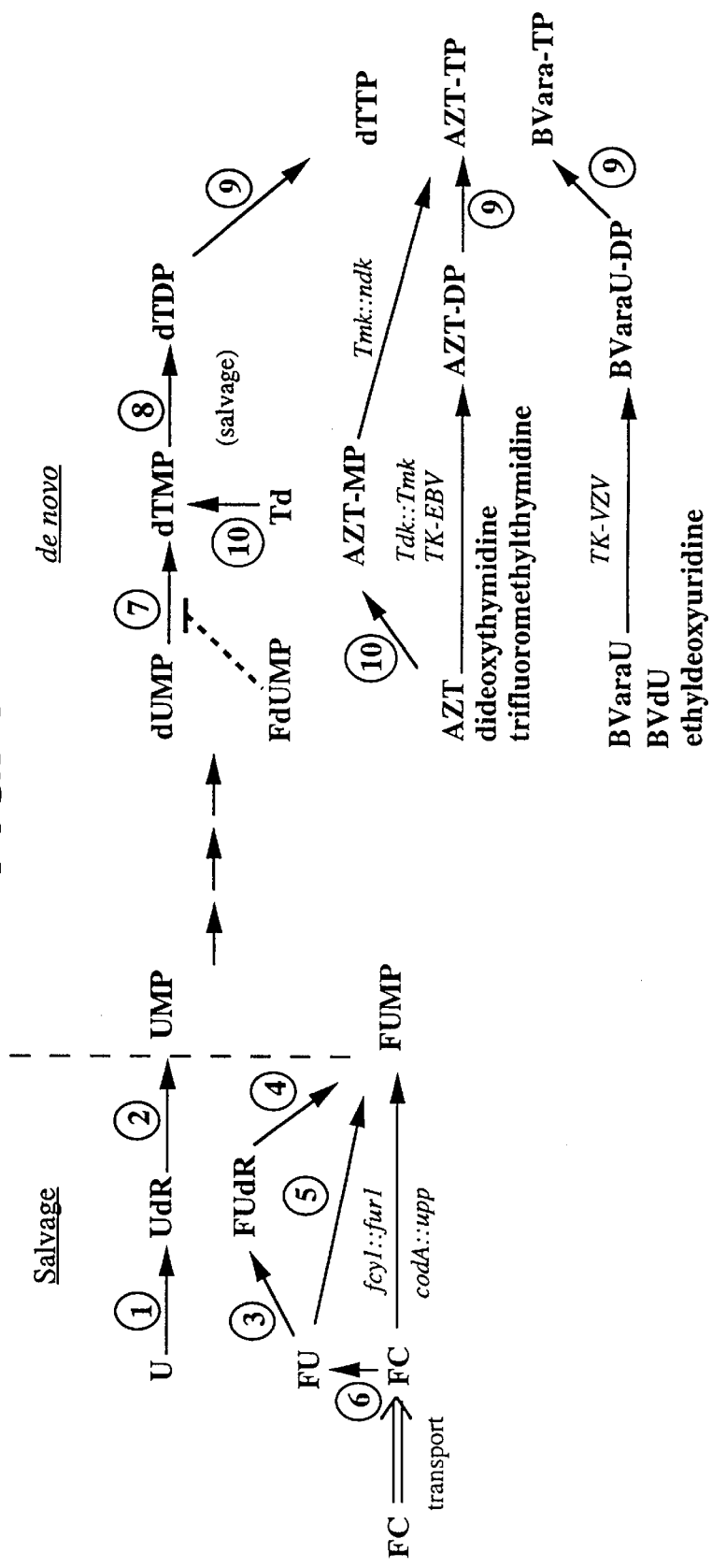
FIG. 1 shows the anabolic pathway for 5-fluorocytosine to give the end product FdUMP, a suicide inhibitor of thymidylate synthase, a key enzyme in the de novo biosynthesis of the thymidylate dTTP. A depletion of dTTP in rapidly dividing cells by the action of FC activated by an enzyme with both CDase and UPRTase activities coded by the new suicide genes of the first group, subject of this invention, induces a so called thymidineless death, possibly by mechanisms related to apoptosis.
Figure 2A:
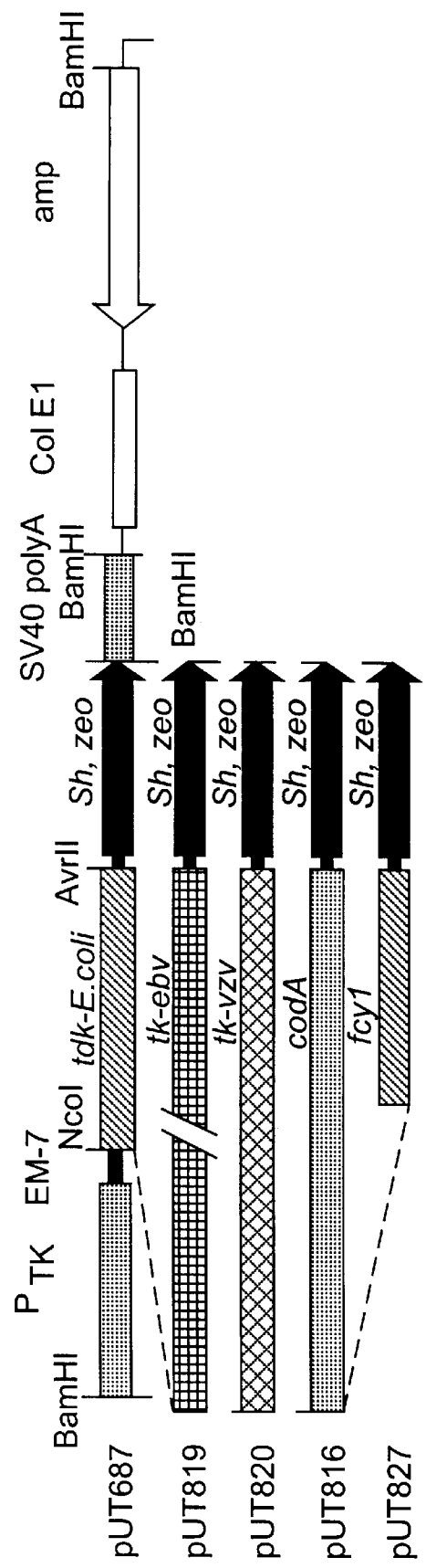
Figure 2B:
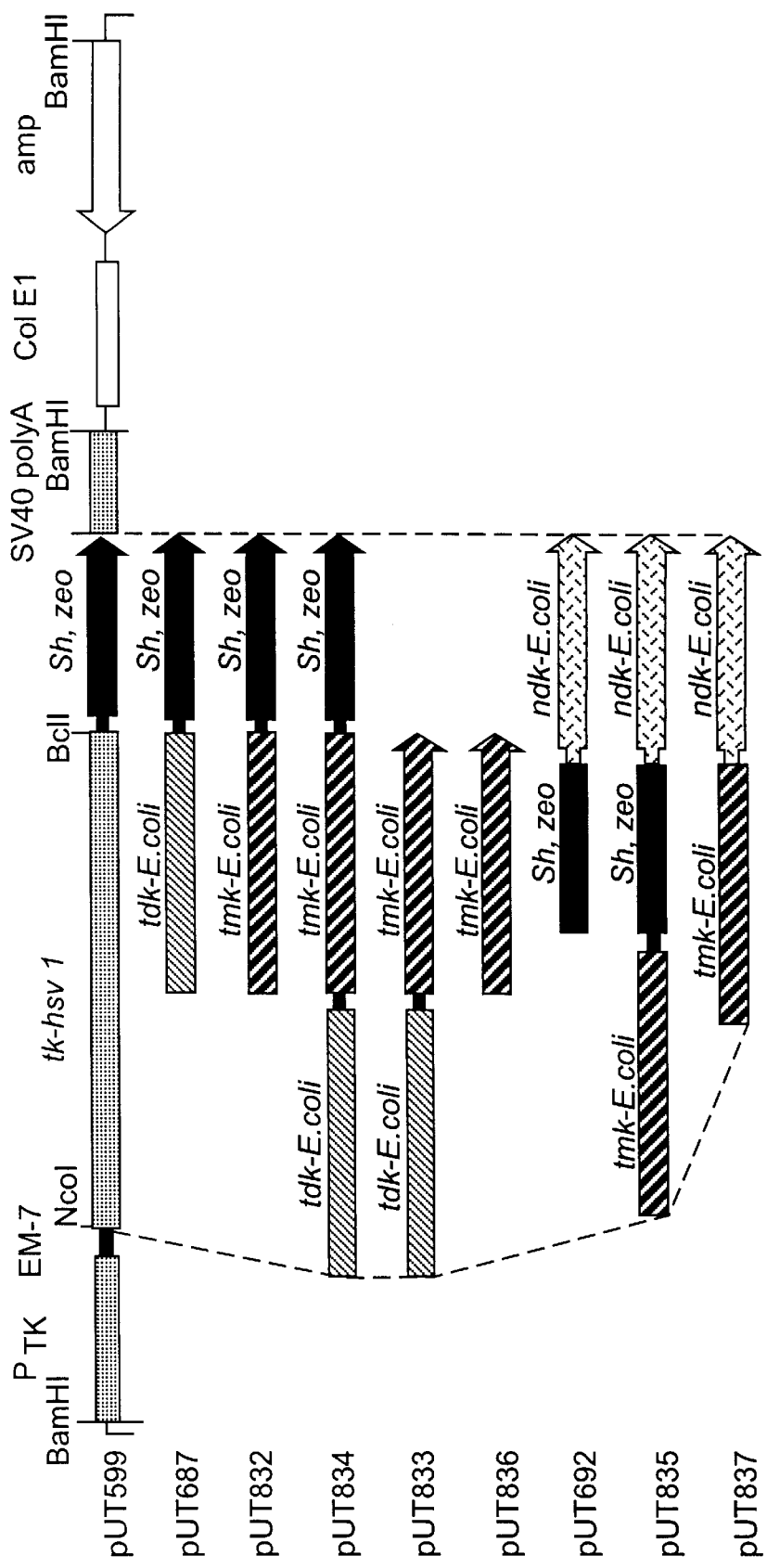
Figure 2C:
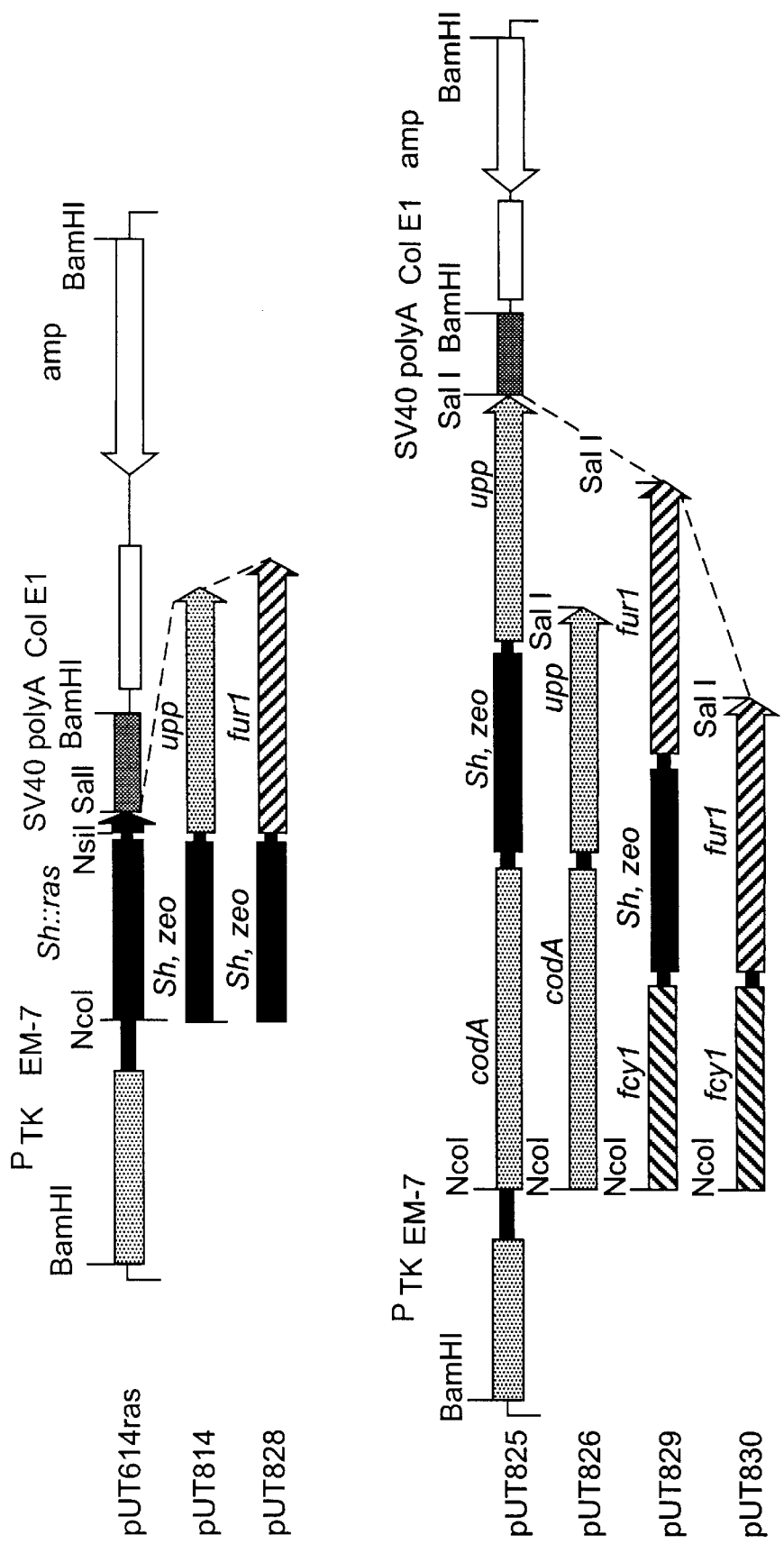
Figure 3A:
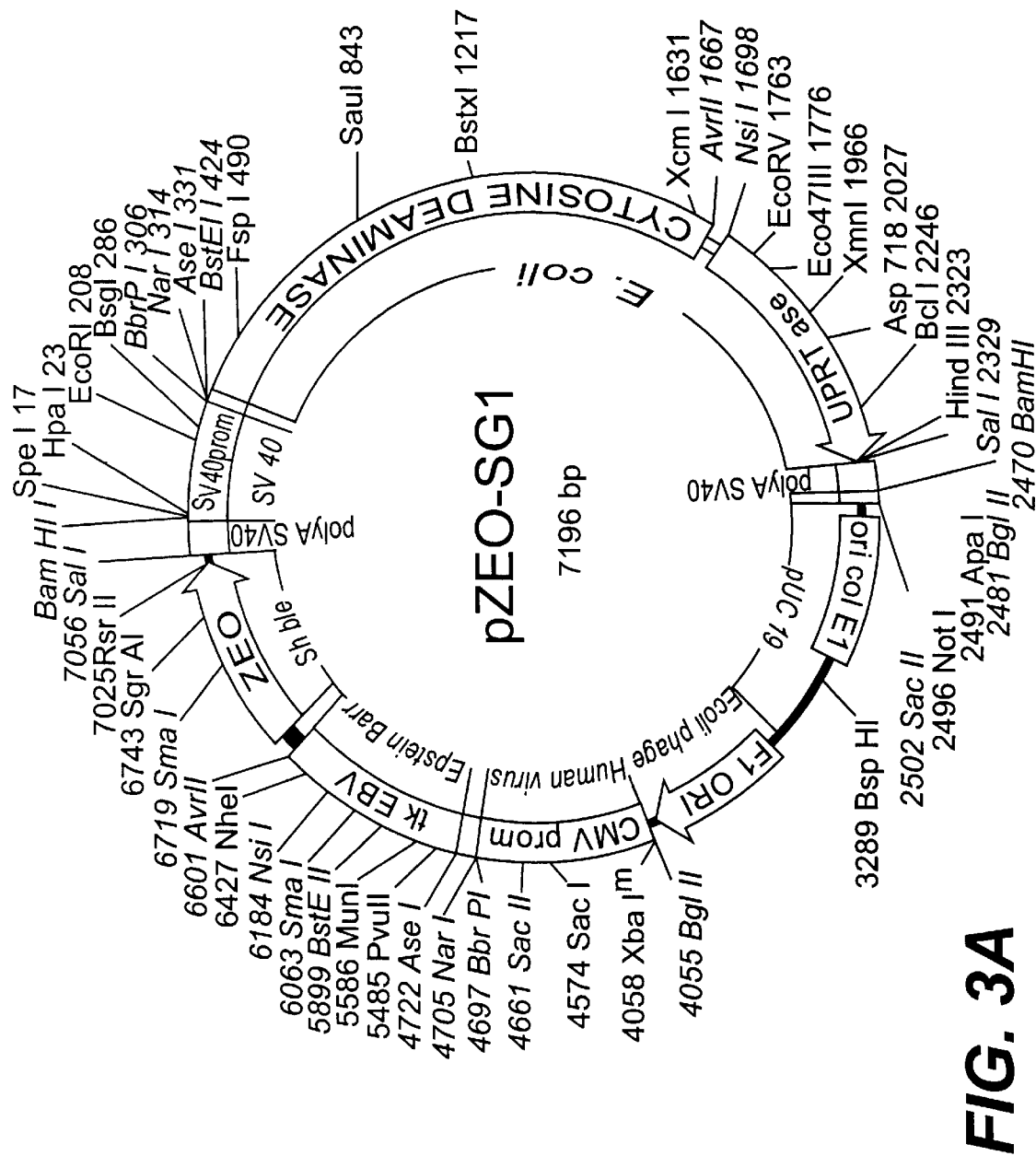
Figure 3B:
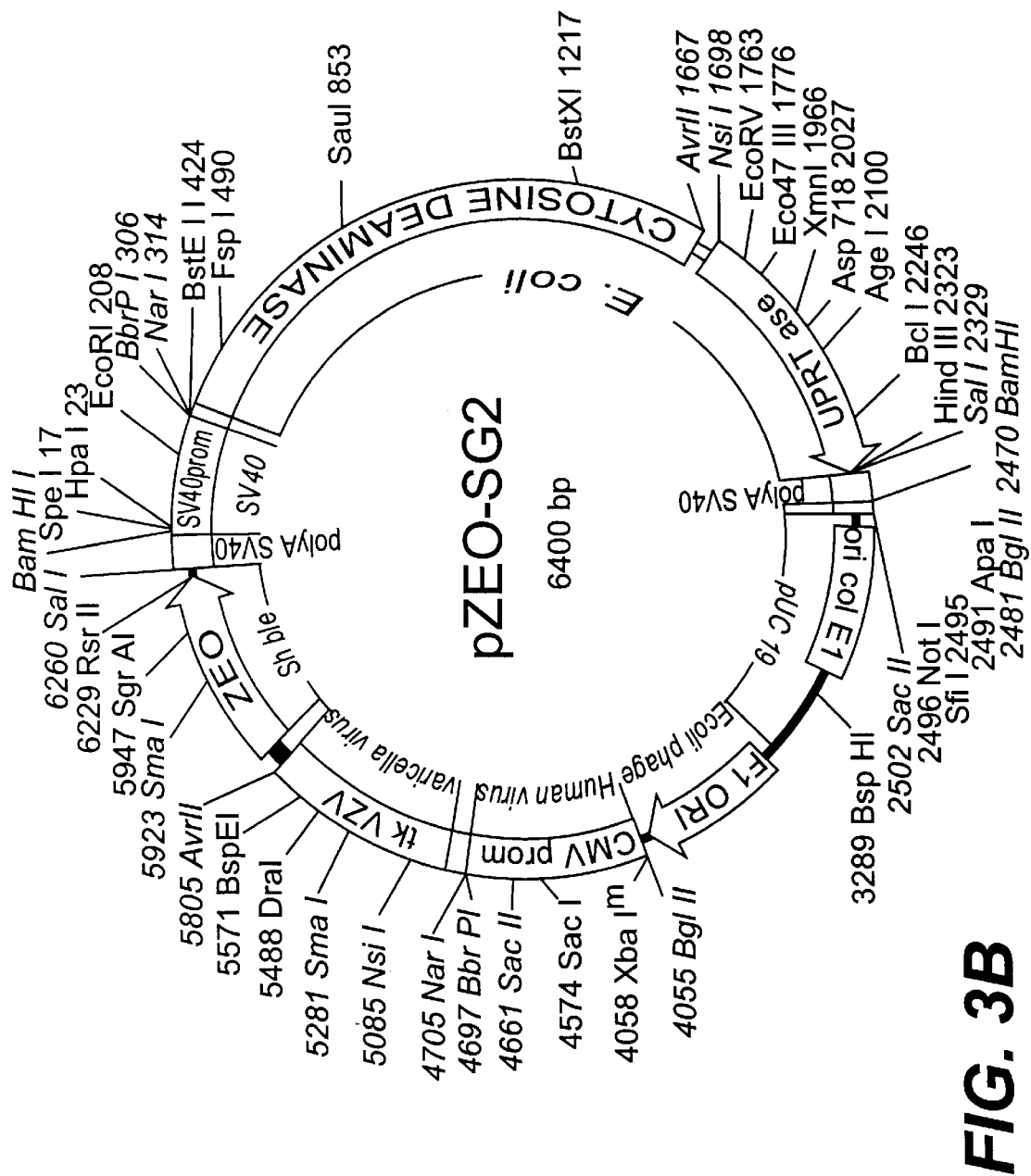
Figure 3C:
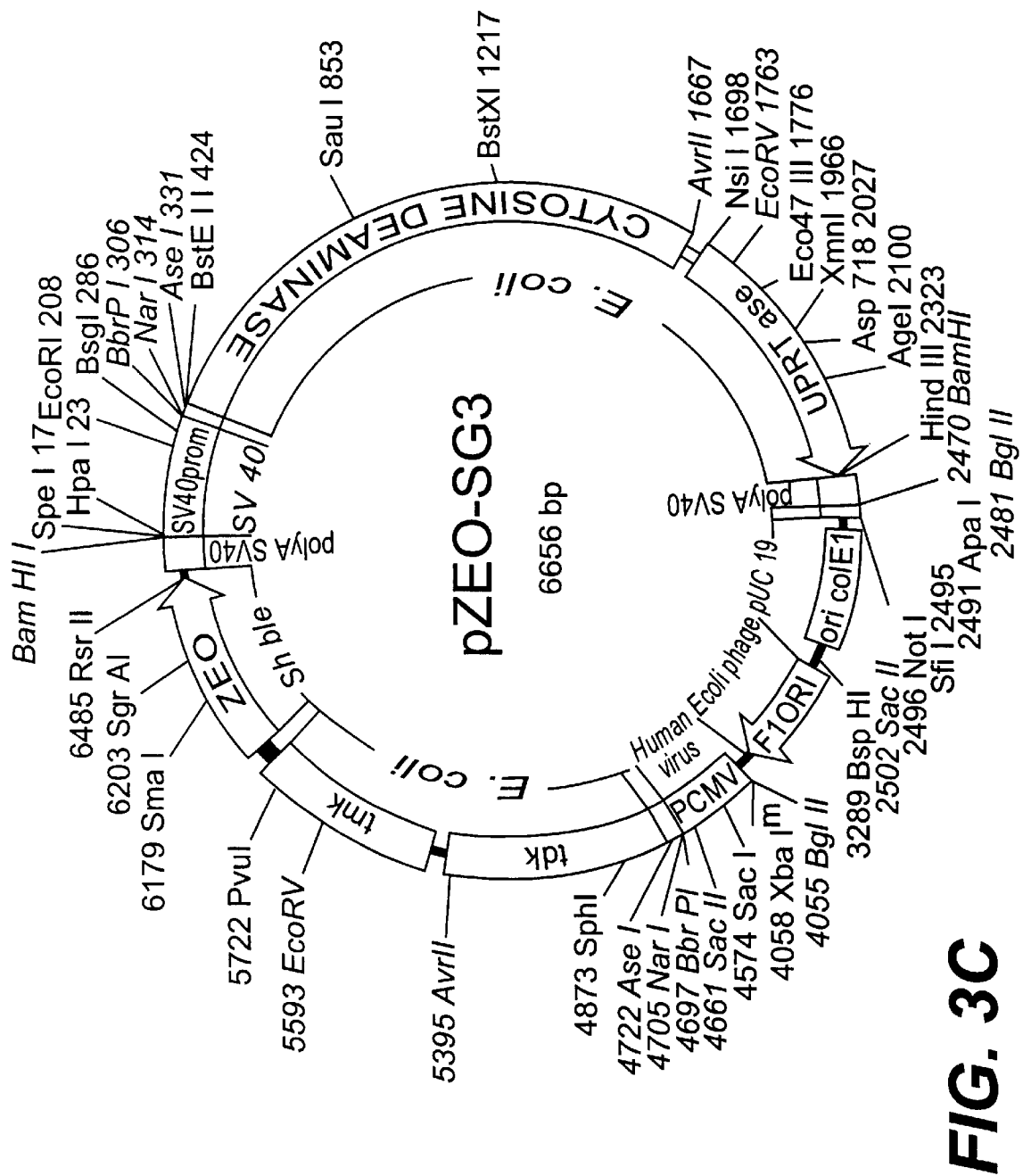
Figure 3D:
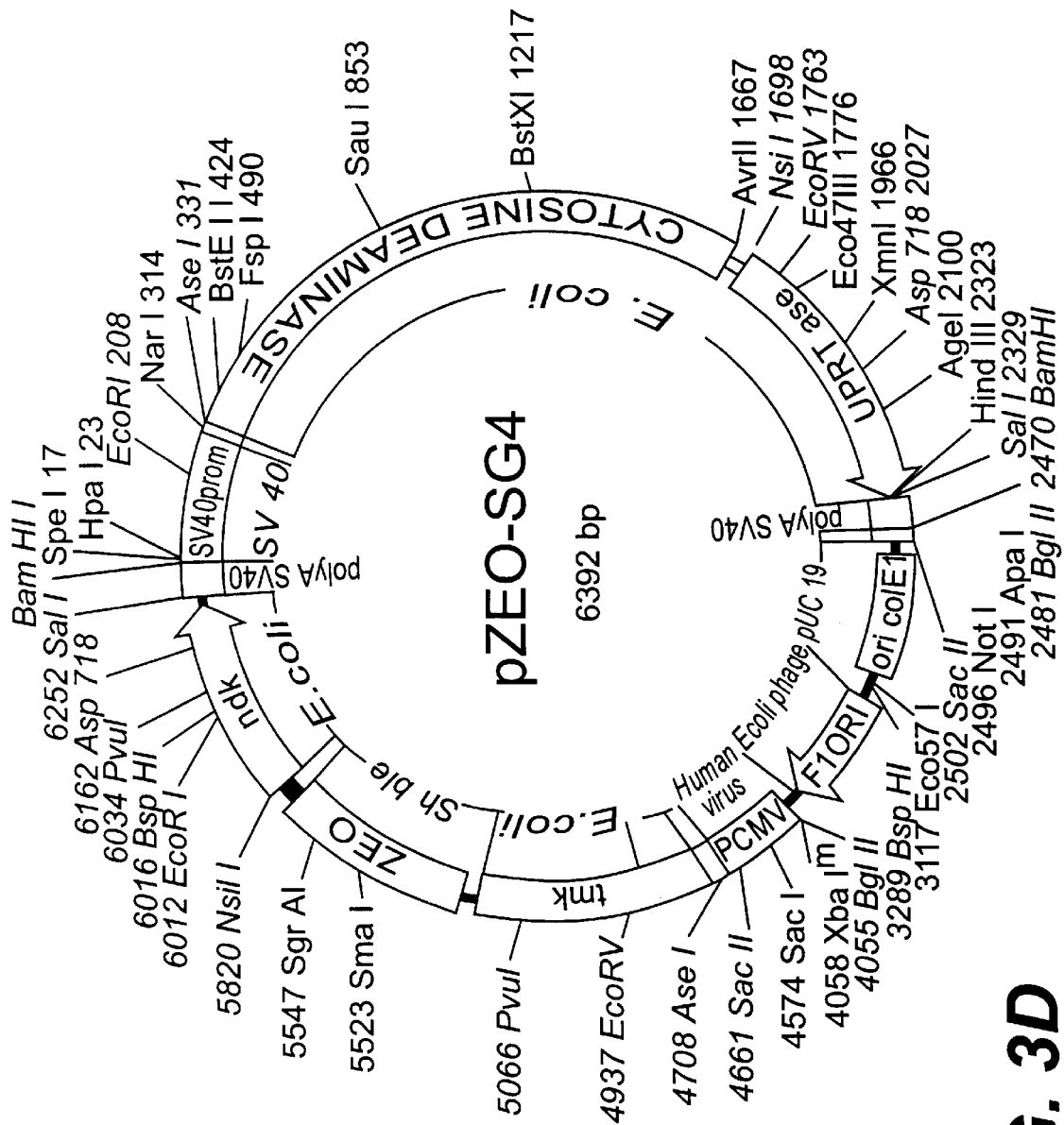

FIGS. 2A–2C illustrate the expression plasmids containing the suicide genes and their filiation.

FIGS. 3A–3D show the maps of expression vectors pZEO-SG1; pZEO-SG2; pZEO-SG3; pZEO-SG4 containing two suicides genes.

The following non limiting examples are presented for purposes of illustration only.

EXAMPLE 1
Isolation of Tdk codA upp mutants of an *Escherichia coli* K12 strain

*Escherichia coli* K12 bacteria metabolize the toxic pyrimidine nucleobase and nucleoside analogs FC, FU and AZT through the action of CDase, UPRTase and thymidine kinase enzymes respectively. Strains deficient for any of these activities are resistant to the corresponding analog. In order to facilitate the cloning of functional tdk$^\pm$ and upp$^\pm$ alleles, a mutant of MC1061, deficient in thymidine kinase activity, was first isolated by selection on AZT containing medium, and from this mutant a UPTRase deficient mutant was in turn isolated by selection of FU resistant clones. A culture of MC1061 grown overnight in LB medium was spread onto M9-CA plates supplemented with 5 $\mu$g ml$^{-1}$ AZT. A MC1061 tdk clone was isolated by picking one of the numerous resistant colonies. A culture of this clone, grown overnight in LB medium, was chilled at 4° C. for 2 hours, and $10^8$ cells were spread onto M9-CA plates supplemented with 30 $\mu$g ml$^{-1}$ 5-fluorouracil. Twenty individual colonies, appearing after 60 hours incubation, were picked and streaked once on the same selective medium. A cell suspension was prepared from grown clones and cells were spotted onto M9-CA plates containing increasing concentrations of 5-fluorocytosine or 5-fluorouracil. One clone resistant to 100 $\mu$g ml$^{-1}$ fluorouracil, 1000 $\mu$g ml$^{-1}$ fluorocytosine was retained and designed CL108. A mutation in the pyrD gene which confers a pyrimidine growth requirement was further introduced by P1 transduction as described by Miller [Miller J. H. Experiments in *Molecular Genetics Cold Spring Harbor*, New York, Cold Spring Harbor Laboratory Press (1972)]. in CL108. The resulting CL109 strain was unable to grow on minimal medium supplemented with cytosine or uracil as the sole pyrimidine source.

The codA gene encoding cytosine deaminase and the cytosine permease codB gene form an operon which is closely linked to the lac operon at 8 minutes of the *Escherichia coli* chromosome [Austin E. A. & Huber B. E. J Bacteriol 175, 3685–6 (1993) ; Danielsen et al. Mol Microbiol 6, 1335–44 (1992)]. *E. coli* strains used for lac Z complementation assays on X-gal plates, such as MC1061, harbor deletions of different length that encompass the codBA operon downstream of the lacZ gene and therefore are devoid of active cytosine transport. In order to construct a MC1061 derivative with an active transport system for cytosine, and hence FC, the region encompassing the promoter and the codB gene from pSD112 was subcloned in pAPT11-, a vector carrying the P15a replication origin [Cornet et al. J Bacteriol 176, 3188–95 1994]. The resulting pAPT codB plasmid, selectable on kanamycin and compatible with the colE1 replicon based plasmids, was introduced into CL108 strain harboring or not one of the pUT plasmids from Table 1. The genotype of the three strains are the following: MC1061 codA codB; CL108:codA codB tdk upp; CL109 : codA codb tdk upp pyrD.

Minimal inhibitory concentrations (MIC) of cells to FC, FU and AZT were determined on M9 plates (Miller J. H. *Experiments in Molecular Genetics* Cold Spring Harbor, New York, Cold Spring Harbor Laboratory Press (1972), supplemented with 0.5% Difco casamino acids, 0.2% glucose, 1 $\mu$g ml$^{-1}$ thiamine and 1.5% Difco agar (M9-CA). When required, antibiotics were added at the following concentrations : ampicillin (Ap, 50 $\mu$g ml$^{-1}$), kanamycin (Km, 25 $\mu$g ml$^{-1}$), tetracycline (Tet, 10 $\mu$g ml$^{-1}$) and zeocin (Zeo, 20 $\mu$g ml$^{-1}$). Zeocin was obtained from CAYLA. Cells from a stock culture were streaked onto plates containing the M9-CA medium and the appropriate antibiotics. After overnight incubation at 37° C., cell suspensions were made by resuspending the surface grown cells in M9 medium to approximately $10^7$ bacteria ml$^{-1}$. Cells were spotted (5 $\mu$l) onto the surface of M9-CA medium containing plates supplemented with increasing concentrations of the analog. The growth of cells was recorded after 48 hours incubation. The results are shown in Table I below.

TABLE 1

Minimal Inhibitory Concentrations to FC and FU ($\mu$g/ml) of *E. coli* MC1061 (codBA)* and CL108 (codBA upp tdk)** harboring one or two plasmids governing the expression of genes from the cytosine salvage pathway

| | FC | | FU | |
|---|---|---|---|---|
| Plasmid | −pAPTcodB | +pAPTcodB | −pAPTcodB | +pAPTcodB |
| —* | 100 | 100 | 0.1 | 0.1 |
| pSD112 (codBA)* | 0.1 | ND | 0.1 | 0.1 |
| —* | >100 | >100 | 100 | 100 |
| pUT816 (codA::Sh)** | >100 | 100 | 30 | 10 |
| pUT814 (Sh::upp)** | 100 | 100 | 0.1 | 0.1 |
| pUT825 (codA::Sh::upp)** | 10 | 0.1 | 0.1 | 0.1 |
| pUT826 (codA::upp)** | 30 | 0.1 | 0.3 | 0.3 |
| pSD112 (codBA)** | >100 | ND | 100 | ND |
| pUT827 (fcy1::Sh)** | >100 | >100 | 100 | 100 |

TABLE 1-continued

Minimal Inhibitory Concentrations to FC and FU (μg/ml) of E. coli MC1061 (codBA)*
and CL108 (codBA upp tdk)** harboring one or two plasmids governing the expression of
genes from the cytosine salvage pathway

|  | FC | | FU | |
| --- | --- | --- | --- | --- |
| Plasmid | −pAPTcodB | +pAPTcodB | −pAPTcodB | +pAPTcodB |
| pUT828 (sh::fur1)** | 100 | 100 | 0.3 | 0.3 |
| pUT829 (fcy1::Sh::fur1)** | 30 | 0.3 | 0.3 | 0.1 |
| pUT830 (fcy1::fur1) | 30 | 0.1 | 0.1 | 0.1 |

Values are means of triplicate experiments.
ND: not determined

EXAMPLE 2
Construction of the coda::upp gene

The sequences of the E. coli codA and upp genes have been recently reported [Danielsen et al. Mol Microbiol 6, 1335–44 (1992); Austin E. A. & Huber B. E. J Bacteriol 175, 3685–6 (1993); Andersen et al. Eur J Biochem 204, 51–6 (1992)]. Using PCR techniques, the coda gene was amplified from the pSD112 plasmid and the upp gene was amplified from the chromosome of strain MC1061 and cloned in pUT687 and pUT614 ras plasmids respectively. These two vectors derive from pUC 19 by replacement of the lacZ promoter and the a peptide sequence by a BamHI fragment carrying the selectable Sh ble gene for zeocin and phleomycin resistance both in E.coli and mammalian cells [Drocourt et al. Nucleid Acids Res 18, 4009 (1990)] [U.S. Pat. No. 5,021,344] [U.S. Pat. No. 5,118,620]. In pUT687, the Sh ble gene is fused in frame on its 5' end to the thymidine kinase gene from Escherichia coli. (see example 5). In pUT614 ras the Sh ble gene is fused in frame on its 3' side to a 47 bp sequence coding for a flexible polypeptide link and the last 12 aminoacids of the human ras gene. The synthetic E. coli EM7 promoter and the mammalian pTK promoter from pMClneo [Thomas K. R. & Capecchi M. R. Cell 51, 503–12 (1987)] in tandem insure expression of the hybrid zeo gene in both E.coli and cultured mammalian cells. The codA gene was PCR amplified with the following primers:

5'end 5'    GTACCATGGTGTCGAATAACGCTTTACAAAC    3' (SEQ ID NO: 1)    and

3'end 5'    CTCCTAGGCGTTTGTAATCGATGGCTTCTGGCTG    3' (SEQ ID NO: 2)

The PCR fragment was cut with NcoI and AvrII and inserted in place of the TK-E.coli containing NcoI-AvrII fragment of pUT687 DNA to give pUT816.

The upp gene was amplified with the polymerase chain reaction (PCR) using the following primers:

5'end .5'    GTCATGCATCAAGATCGTGGAAGTCAAACACCCA    3' (SEQ ID NO: 3)    and

3'end 5'    CTGGTCGACAAGCTTATTTCGTACCAAAGATTTTGTCACC    3' (SEQ ID NO: 4).

The resulting PCR fragment was cut with NsiI and SalI and inserted in pUT614ras in place of the ras containing NsiI-SalI fragment to give pUT814. The use of CL109 provided a positive selection method for the cloning of codA and upp respectively. Transformants harboring the codA⁺:: Sh expressing pUT816 plasmid were selected from CL109 on medium containing cytosine as the sole pyrimidine source whereas transformants harboring the Sh ::upp⁺ expressing pUT 814 plasmid were isolated on a uracil containing medium. The two plasmids pUT816 and pUT814 were next recombined in vitro by ligating a BglII-SgrAI fragment from one plasmid to the complementary BglII-SgrAI fragment from the other to give pUT825. The resulting codA::sh::upp gene codes for a hybrid protein with three distinct domains separated by flexible hinges (FIGS. 2A–2C). A unique protein band of 75 kD, slighty inferior to the 80 kD expected size for the product of the codA::Sh::upp gene was detected by Western blot against an Sh protein antiserum of separated proteins from strain CL108 (pUT825). The functionality of the codA::Sh::upp fusion gene is attested by the ability of pUT825 to allow CL109 bacteria to grow with either cytosine or uracil as pyrimidine source and to sensitize cells to FC and FU (Table 1). In addition pUT825 confers, on recipient cells, a resistance of up to 200 ug ml⁻¹ of zeocin, identical with resistance levels attained with any other plasmids from FIGS. 2A–2C. This is a hundred fold increase in resistance compared to untransformed strains.

Finally the codA::upp gene (pUT825) was constructed by replacing the AvrII-NsiI fragment containing the Sh ble gene from pUT829 by a double stranded oligonucleotide coding for a flexible peptidic hinge.

5' CTAGGGATCTCAGGCCTTAATGGCGTATGCA 3' (SEQ ID NO: 5)
   CCTAGAGTCCGGAATTACCGCAT   (SEQ ID NO: 6)

EXAMPLE 3
Construction of the fcy1::fur1 gene

The sequences of the fcy1 and fur1 genes of S.cerevisiae encoding the cytosine deaminase and uracil phosphoribosyltransferase have been reported [(EP 90306131.5; Kern et al. Gene 88,149–57 (1990)]. Both genes have been amplified using PCR techniques from yeast DNA of strain OL1. NcoI-AvrII and NsiI-SalI restriction sites were created at the 5' and 3' termini of the coding sequence of the fcy1 and fur1 genes respectively using the oligonucleotide primers:

5'end 5'   GTACCATGGTGACAGGGGGAATGGCAAGCAA 3' (SEQ ID NO: 7)   and

3'end 5'   TCCCTAGGGCCTCACCAATATCTTCAAACCAATCCTG 3' (SEQ ID NO: 8)   for fcy1

5'end 5'   TGGATGCATGAACCCGTTATTCTTTTTGGCTTCT 3' (SEQ ID NO: 9)   and

3'end 5'   TCGAGGTCGACTTTAAACACAGTAGTATCTGTCACCAAA 3' (SEQ ID NO: 10)   for fur1.

The fcy1 gene was then ligated into pUT687 within the NcoI and AvrII sites and the fur1 gene into pUT614 ras within the NsiI and SalI sites to generate plasmids pUT827 and pUT828 respectively. E.coli transformants for pUT827 carrying fcy1::Sh were selected in minimum medium containing cytosine as sole pyrimidine source whereas transformants for pUT828 carrying Sh::fur1 were selected in minimum medium containing uracil.

The two genes, fcy1::Sh and Sh::fur1, were next recombined in a unique gene fcy1::Sh::fur1 by ligating a NcoI-SgrAI fragment from pUT827 to the complementary NcoI-SgrAI fragment from pUT828, giving plasmid pUT829. The functionality of the hybrid gene fcy1::Sh::fur1 was controlled by the ability of strain CL109, transformed with pUT829, to grow with either cytosine or uracil as sole pyrimidine source and by the sensitivity of strain CL108 transformed with pUT829 to FC and FU (Table 1).

Finally the fcy1::fur1 gene was constructed similarly to the codA::upp gene by replacing a AvrII-NsiI fragment from pUT829 by a double stranded oligonucleotide coding for a flexible peptidic hinge (described in example 2) to give pUT 830.

Bacterial strains transformed by pUT829 and pUT830 were assayed for CDase and UPRTase activities. Cells collected from 20 ml of an overnight culture in LB medium. were washed once with an equal volume of cold 20 mM Tris-HCl at pH 7.5 and then resuspended in 1 ml of the same buffer containing 1 μg ml$^{-1}$ lysozyme. After 10 minutes on ice, the cell suspension was subjected to two freeze-thaw cycles and then sonicated five times in bursts of 30 seconds. Cell debris and intact cells were removed by centrifugation and supernatants were used for enzyme assays. In vitro assays for cytosine deaminase and UPRTase were performed using procedures slightly modified from described methods. [Andersen et al, (1989)]. Standard reaction mixtures contained in a 100 μl volume : 50 mM Tris-HCl pH 7.5; 1 mM DTT; 10 μl cell extract for both activities and in addition 5 mM cytosine for cytosine deaminase and 5 mM uracil ; 5 mM MgCl$_2$, 2 mM PRPP (Sigma) for UPRTase. The enzymatic reactions were stopped after 2 hours at 30° C. in ice cold. Aliquots of 10 μl were chromatographed on polyethylenimine-impregnated cellulose thin layer plates (Merck) with premarked spots which contained 4 μg each cytosine, uracil and UMP as markers. The thin layer plates were developed in water for a resolutive separation of cytosine and uracil from UMP, in 1-butanol/water (86/14) for a clear distinction between uracil and cytosine. The presence of spots corresponding to reaction products visualised under UV light were taken as an indication of enzyme activity. The appearance of uracil from cytosine and UMP from uracil were observed solely in extracts of E.coli cells transformed by pUT829 and pUT830.

EXAMPLE 4

Cloning of the Escherichia coli tmk gene

The genetic location of tmk, the gene coding for dTMP kinase has been mapped to approximately 24 minutes on the E.coli chromosome [Binkley J. P. & Kuempel P. L. J. Bacteriol 168, 1457–8 (1986)]. From the numerous nucleotide sequences deposited at the GenBank, lying at 24 to 25 minutes on the genomic map, a single unsequenced gap between the acpP and the holB genes could possibly enclose the tmk gene. Consequently the acpP-holB intergenic region was cloned by PCR amplification from the Kohara phage λ E9G1 [236] [Kohara et al. Cell 50, 495–508 (1987)]. The primers used were 5' end 5'   ATTTCGAATTCCCTCCCTGGAGGACAAACGTGT 3' (SEQ ID NO: 11)

3' end 5'   CCACCGGTACCATCTCATGCGTCCAACTCCTTC 3' (SEQ ID NO: 12)

The 5' end primer contained twenty-five bases homologous to the 3' end of the published acpP sequence (bases in boldface) [Rawlings M. & Cronan J. J. J. Biol Chem 267,5751–4 (1992)] and extra bases to generate an EcoRI site. The 3' end primer contained twenty-six bases homologous to the holB sequence [(Carter et al. J. Bacteriol 175, 3812–22 (1993); Dong et al. J. Biol Chem 268,11758–65 (1993)] around the ATG start codon (bases in boldface) and extra bases to generate an Asp718I site.

The PCR generated DNA fragment (~ 4 kb) was digested by EcoRI and Asp718I and ligated into PZEO SV1 (GenBank accession number L36849; commercialised by CAYLA) digested by EcoRI and Asp718I. After transformation of E.coli by the ligation mixture, it was not possible to obtain transformants harboring the expected size of the recombinant plasmid suggesting that the amplified region was somehow toxic or lethal to E.coli. The same result was obtained by cloning the PCR amplified product reduced to a 2.5 kb BglII/Asp718I fragment into pUT58 (commercialised by CAYLA, digested by BglII and Asp718I). Further subcloning experiments of a 1.6 kb BglII/PstI fragment into pUT 106 (commercialised by CAYLA ; digested by BglII and PstI) or a 0,9 kb PstI/Asp718I fragment into PAPT 110 ( digested by PstI and Asp718I) gave rise to stable recombinant plasmids respectively named pUT 126 and pUT 125.

Primers were synthesized on the basis of the DNA sequences of the cloning vectors pUT106 and pAPT110 to initiate sequencing of the inserts from PstI to Asp718I in pUT 125 and from PstI to BglII in pUT126. Sequences obtained with these primers were used to design a second set of primers and to derive additional sequence data. This strategy was used to gain double-stranded sequence data for 1,288 bp of DNA. The sequence contained a coding region of 642 nucleotides that encodes approximately a 25 kD protein. When compared to the amino acid sequences of the human, yeast, vaccinia virus, variola virus and african swine fever virus dTMP kinases, the E.coli deduced protein showed high homology with them indicating that the E.coli dTMP kinase tmk gene was cloned. The stop codon of E. coli tmk gene overlaps with the proposed initiation codon of holB [(Carter et al. J. Bacteriol 175, 3812–22 (1993); Dong et al. J. Biol Chem 268,11758–65 (1993)] suggesting that the two genes are translationally coupled and exist in an operon. Flanking the tmk gene, the sequence of an upstream open reading frame was analysed for similarity to known proteins in the GenBank data base. The ORF upstream of tmk showed 100% amino acid (and nucleic acid) identity with an E.coli hypothetical protein mentionned in pabc 3' region previously mapped to 25 minutes on the E.coli chromosome [Green et al. J Bacteriol 174, 5317–23 (1992)]. Based on these data it was concluded that the E.coli tmk gene is located just upstream from the holB gene (24.95 min) and downstream from the genetic sequence (clockwise on the genetic map) acpP-fabF-pabC-orfX.

To facilitate subcloning experiments the E.coli tmk gene was modified at both 5' and 3' ends of the gene by PCR. NcoI and MscI sites were introduced at the beginning of the tmk coding sequence for respectively optimal eukaryotic initiation sequence and construction of 5' gene fusions. The C-terminal region was modified by introducing a MluI site just before the stop codon for construction of 3' gene fusions and RsrII site just behind the modified stop codon for easier subcloning. The tmk sequence from pUT 125 was used as a template for the PCR reaction with the following primers:

5' end 5'   GTACCATGGCACAGCTATATTTCTACTAT   3' (SEQ ID NO: 15)

3' end 3'   CTGGATCCCTAGGTCGTGGCGATGCCTTTCCTGAATAGCC   3' (SEQ ID NO: 16)

EXAMPLE 5

Construction of the tdk::tmk and tmk::ndk genes

The sequence of the E.coli tdk gene has been recently reported [Bockamp et al. Gene 101, 9–14 (1991); Black M. E. & Hruby D. E. Mol Microbiol 5, 373–9 (1991)]. The tdk coding region was PCR amplified using E.coli DH5α chromosomal DNA as template and the following primers (homologous bases in boldface).

The resulting PCR fragment was cut with NcoI and BamHI and inserted in place of the TK-HSV1 containing the NcoI-BclI fragment of pUT 599 DNA (prepared from a dam⁻ strain) to give pUT 687.

The PCR regenerated DNA fragment containing the modified E.coli tmk gene (example 4) digested with NcoI and MluI (treated with Klenow enzyme) was inserted in pUT655 (derived from pUT599, commercialised by CAYLA) digested by NcoI and PvuII to give pUT832.

The MscI-RsrII fragment from pUT 391 (example 4) containing the E.coli tmk gene was inserted in place of the Sh ble gene containing the MscI-RsrII fragment of pUT687 to give pUT833.

The PCR regenerated DNA fragment containing the modified E.coli tmk gene (example 4) digested by NcoI and RsrII was inserted in place of the TK HSV1-Sh ble gene fusion containing the NcoI-RsrII fragment of pUT 599 to give pUT 836.

5' end 5'   AGGACCATGGCCAGAAGTAAGTATATCGTCATTGAGGGG   3' (SEQ ID NO: 14)

3' end 5'   TGCACGGACCGTTACGCGTCCAACTCCTTCACCCAGTGG   3'

The enzyme activity encoded by the E. coli tmk gene was demonstrated by functional complementation of a yeast dTMP kinase temperature-sensitive mutant (cdc8) at a non-permissive temperature.The PCR regenerated DNA fragment containing the modified tmk gene was digested by MscI and RsrII and ligated into the E.coli-yeast shuttle vector pUT 377 (commercialised by CAYLA) digested by MscI and RsrII. The ligation mixture was used to transform E.coli for preparation of recombinant plasmid DNA (pUT 391). Saccharomyces cerevisiae CMY616 strain (MAT a ura3 leu2 his7 cdc8 can 1-100 ) was transformed with pUT391. All the ura⁺ transformants selected at 22° C. were then replicated to YEPD plates and screened for a temperature resistant phenotype at 32° C. All ura⁺ transformants displayed the tmk⁺ phenotype. Some of them were streaked out on non-selective plates to obtain ura⁺ colonies that became temperature sensitive (tmk⁻) indicating that the temperature property was mediated by the presence of the plasmid pUT391.

The EcoRV-NotI fragment from pUT 832 containing the E.coli tink-Sh ble fusion was inserted in pUT 833 cut with EcoRV and NotI to give pUT 834.

The sequence of the E.coli ndk gene has been recently reported [Hama et al. Gene 105, 31–6 (1991)]. The ndk coding region was amplified using PCR techniques from E.coli DH5a chromosomal DNA with the following primers (homologous bases in boldface).

5' end 5'   CCATATGCATGGCTATTGAACGTACTTTTTCCATCATCAAA   3' (SEQ ID NO: 17)

3' end 5'   TGTGTCGACTTAACGGGTGCGCGGGCACACTTCGCC   3' (SEQ ID NO: 18)

The resulting PCR fragment was cut with NsiI and SalI and inserted in pUT 614ras in place of the ras containing NsiI-SalI fragment to give pUT 692.

The NcoI-SgrAI fragment from pUT 832 containing the E.coli tmk-Sh ble fusion was inserted in pUT 692 cut with NcoI and SgrAI to give pUT 835.

In pUT 837 the E.coli tmk gene is fused in-frame on its 3' side to a 18 bp sequence coding for a flexible polypeptide link and the ndk gene. To facilitate this construction a new 3' end PCR primer was used to modify the tmk coding sequence from pUT 125 (homologous bases in boldface).

5' end 5' AGGACCATGGCCAGAAGTAAGTA
TATCGTCATTGAGGGG 3' (SEQ ID NO: 19)
(example 4)
new 3' end 5'GACATGCATCCAGGTCCCTGGTCCA
ACTCCTTCACCCAGTGGGTC (3' SEQ ID NO: 20)

The PCR generated DNA fragment containing the modified tmk gene on its 3' side was digested by NcoI and NsiI and ligated into the vector pUT 692 cut by NcoI and NsiI to give pUT837.

The functionality of the tdk hybrid genes was demonstrated in the tdk⁻ recipient strain CL108 which became hypersensitive to AZT upon transformation by a tdk expressing plasmid. The functionality of the tmk hybrid genes was demonstrated in the E.coli tmk recipient strain TD205 which acquired resistance to 30 µg ml-1 bromodeoxyuridine, a resistance phenotype associated to the wild-type tmk allele in the particular strain TD205 [Binkley J. P. & Kuempel P. L. J Bacteriol 168, 1457–8 (1986)].

EXAMPLE 6
Cloning of the tk-VZV and the tk-EBV genes.

The TK genes of Herpes simplex virus display both thymidine and thymidylate kinase activities. Similarly, kinetic studies and computer comparison of amino acid sequences reveals that Varicella-Zoster (tk-VZV) and Epstein-Barr (tk-EBV) genes could possess high thymidylate kinase activity [Baer et al. Nature 310, 207–211 (1984); Littler et al. EMBO J.5, 1959–1966 (1986)].

In order to determine whether the TK gene of these two viruses phosphorylates. AZT-MP, they were cloned and expressed in the E.coli strain CL108. The TK-VZV and TK-EBV genes were amplified respectively using PCR techniques from a 2.2 kb EcoRI-BamHI fragment inserted into mp1b M13 DNA (gift from Dr R. Gaillard, Burroughs-Wellcome Co, USA) and plasmid pUC8X containing the Epstein-Barr virus BXLF1 open reading frame provided by Dr Y. Connolly from Paterson Institute for Cancer Research, UK. The nucleic acid sequences of the genes being known [Mori et al. *Intervirology* 29, 301–310 (1988); Robertson G. & Whalley J. M. Nucl. Acids Res. 16, 11303–11317 (1988)], both genes were amplified by using the following primer couples:

5'end 5' GTACCATGGCATCAACGGATAAAACCGATGTAAAAATG 3' SEQ ID NO:21 and

3'end 5' CGCCCTAGGGAAGTGTTGTCCTGAAC 3' (SEQ ID NO:22) for tk-VZV

5'end 5' GGGAGCGCTGGATTTCCAGGAAAG 3' (SEQ ID NO:23) and

3'end 5' AAGCCTAGGTCCCGATTTCCCCTCTC 3' SEQ ID NO:24) for tk-EBV.

The amplified fragment containing TK-*E-coli* was cut with NcoI and AvrII and inserted in place of the TK-HSV containing the NcoI-AvrII fragment of the pUT687 plasmid to create pUT820 DNA.

The TK-EBV gene was cloned similarly into the pUT687 to produce pUT819 plasmid. However, because the TK-EBV contains an internal NcoI site, the PCR product was digested with Eco47III and AvrII. The insert was positionned in place of the *E.coli* tdk gene containing the NcoI-AvrII fragment of pUT687 plasmid by pre-treating the DNA vector with Klenow polymerase after the NcoI digestion.

Transformants harboring the tk-VZV::Sh and tk-EBV::Sh fusions were selected from CL108 on a rich medium containing 200 µg ml⁻¹ zeocin. Expression of the hybrid proteins was assessed by western blot against an Sh protein antiserum which detected 50 kD and 80 kD bands respectively. The functionality of the tk genes was verified by the incapacity of the transformants to grow on LB medium supplemented with 10 µg/ml AZT.

EXAMPLE 7
Construction of expression vectors carrying two suicide hybrid genes

Step 1 : construction of expression vectors carrying one suicide hybrid gene.

The construction of expression vectors carrying two suicide hybrid genes comprised two steps. In a first step, a series of plasmids containing one suicide gene fused in frame with the Sh ble gene were constructed. All these plasmids derived from pUT 809, a plasmid obtained by ligating the 2238 bp AseI BamHI fragment of pZEO SV1 (distributed by Cayla and Invitrogen, GenBank n°360849) carrying the colE1 replicon, the phage F1 origin and the enhancer and promoter of the immediate early gene of human cytomegalovirus with the 1764 bp AseI BamHI of pUT 599 (CAYLA catalog) bearing the tk-HSV1::Sh ble gene. Competent CL108 tdk- (isolated in example 1) were transformed with the ligation mixture and appropriate dilution plated onto LB+zeocin (20 µg/ml). All zeocin resistant clones were unable to grow on LB medium+AZT (10 µg/ml) and contained the expected pUT 809 as confirmed by DNA sequence analysis of their plasmids.

Then the tk-HSV1::Sh ble gene of the pUT599 was successively replaced by the following four genes : tk-EBV::Sh, tk-VZV::Sh genes (both described in example 6), tdk::tmk::Sh, tmk::Sh:ndk (both described in example 5).

The fusion genes, tk-EBV::Sh tk-VZV::Sh and tdk::tmk::Sh were isolated as a BbrPI-RsrII fragment from respectively pUT819, pUT820 and pUT834 (FIGS. 2A–2B) and inserted in place of tdk-HSV1::Sh containing the BbrPI-RsrII fragment of pUT809 to give respectively pUT838, pUT839 and pUT840. The tdk::tmk::Sh gene was isolated as a AseI-SalI fragment of pUT835 (FIG. 2B) which was substituted for the tk-HSV1 ::Sh containing AseI-SalI fragment of pUT809 to give pUT841. As with pUT809, the three recombinant plasmids pUT837, pUT838 and pUT839 render the Cl108 host highly sensitive to AZT, and resistant to Zeocin.

Step 2 : Construction of expression vectors carrying two suicide hybrid genes

The BamHI fragment encoding the CDase and UPRTase hybrid proteins isolated from pUT 826 (FIGS. 2A–2C), was inserted in the unique BamHI site of pUT838, pUT839, pUT840 and pUT841 to give respectively pZEO-SG1, pZEO- SG2, PZEO-SG3 and pZEO- SG4 (FIGS. 3A–3D). The bacterial host, CL108, harboring one of the three recombinant plasmids pZEO-SG1, pZEO-SG2 and pZEO-SG3 is sensitive to FC, FU and AZT and is able to grow on LB medium containing 200 µg/ml of Zeocin.

The complete nucleotide sequences of pZEO-SG1, pZEO-SG2, pZEO- SG3 and pZEO- SG4 have been deposited with GenBank (USA) under the accession numbers L37432; L37440; L37441and L37442 respectively.

EXAMPLE 8

Murine melanoma B16 cell lines expressing the codA::sh-::upp gene or the fcyl::sh::furl gene are sensitive to FC toxicity.

The highly metastasic murine melanoma B16 cell line BL6 provided by Dr S. Cros (Laboratoire de Pharmacologie et de Toxicologie Fondamentales, CNRS, France) was used to determine the efficiency of the various constructs in a tumor cell line. Parent and transfected clones were grown in a MB16 medium i.e. a L-glutamine-containing RPMI1640 medium (GIBCO BRL) supplemented with 10% horse serum (GIBCO BRL) and 2g/l sodium bicarbonate (SIGMA), and adjusted to pH 7.0.

The cell transfection protocol was as follows: subconfluent cells were incubated at 37° C in 35 cm-diameter Petri dishes with one milliliter of serum-deficient MB16 medium containing 5 pmol DNA and 10 μg polybrene (SIGMA). After a 20 h incubation, cells were treated during 3 minutes at 25° C. with a 30% DMSO (SIGMA) suspension in the serum-deficient MB16 medium. Finally cells were washed and incubated 72 h in MB16 medium and trypsinized. The cells were seeded in two separate 10 cm-diameter Petri dishes and 50 μg/ml zeocin (CAYLA) was added. After 20–25 days, foci of zeocin-resistant cells could be visually ascertained. Three clones were picked for each construct, transferred to a 24-well plate and incubated for 7 days in medium containing zeocin (100 μg/ml) before testing. The resistance to zeocin allowed the selection of transfected clones.

The in vitro sequential conversion of radiolabeled cytosine to uracil, and then of uracil to uracil monophosphate by cell lysates, was measured in order to demonstrate both cytosine deaminase and uracil phosphoribosyltransferase activities. This assay was performed according to described methods [Mullen, 1992; Natalini et al. J. Biol. Chem. 254, 1558–1563 (1979)]: about $10^6$ cells were washed and resuspended in 10 μl of 100 mM Tris.HCl pH7.8/1 mM EDTA/1 mM dithiothreitol. After five freezing-thawing cycles, 10 μl of cell lysate were combined with 10 μl of both ($^3$H)cytosine and ($^{14}$C)uracil, then incubated for 4 hours. Samples, mixed with 0.4 mg/ml unlabeled cytosine, uracil and UMP (all from SIGMA), were placed on thin-layer chromatography sheets (Kodak chromatogram sheet 13254) and developed in a mixture of 1-butanol (85%)—water (15%). The radioactivity recovered from cytosine, uracil and UMP bands cut under short-wave UV irradiation were assayed in a scintillation counter.

Table 2 shows the complementary influences of both activities on toxicity to 5-FC. It worth mentioning that expression of these activities had no obvious deleterious effects on cells in the absence of 5-FC.

TABLE 2

Minimal Inhibitory Concentrations to AZT and FC (μg/ml) of B16 melanoma cells transfected by plasmids governing the expression of suicide genes from pyrimidine pathways.

| Plasmid | AZT | FC |
|---|---|---|
| — | 300 | >500 |
| pUT687 (tdk::Sh) | 300 | ND |
| pUT832 (tmk::Sh) | 10 | ND |
| pUT834 (tdk::tmk::Sh) | 1 | ND |
| pUT816 (codA::Sh) | ND | 250 |
| pUT814 (Sh::upp) | ND | 500 |
| pUT825 (codA::Sh::upp) | ND | 5 |
| pUT827 (fcy1::Sh) | ND | 500 |
| pUT828 (Sh::fur1) | ND | 500 |
| pUT829 (fcy1::Sh::fur1) | ND | 10 |

Values are means of triplicate experiments.
ND: not determined

EXAMPLE 9

Murine melanoma B16 cell lines expressing the tdk::tmk::Sh gene are sensitive to AZT toxicity.

Melanoma cells were transfected as described in example 8 by selecting in zeocin-containing MB16 medium. Table 2 shows that the presence of thymidylate kinase activity increased the metabolization of AZT by the salvage pathway up to 300 (tdk::tmk::Sh) and 15 (tk-EBV::Sh) fold respectively.

EXAMPLE 10

Murine melanoma B16 cell lines expressing the tdk::Sh-::tmk gene or the tk-EBV::sh gene simultaneously with the codA::upp gene are hypersensitive to AZT and FC toxicities B16 cells have been transfected as described in example 8 by selecting in zeocin-containing MB16 medium. The plasmids used were constructed to block the de novo pathway with the codA::upp fusion (see example 2) in the presence of 5-FC in order to lower the intracellular pool of dTTP and consequently amplify the toxic effect of AZT. Table 3 indicates that such a concept allows considerable disminishment of the lethal doses of AZT.

TABLE 3

Minimal Inhibitory Concentrations to AZT and BVaraU (μg/ml) in the presence of 2.5 μg/ml FC of B16 melanoma cells transfected by plasmids governing the expression of suicide genes from pyrimidine pathways.

| | AZT | | BVaraU | |
|---|---|---|---|---|
| Plasmid | −FC | +FC | −FC | +FC |
| pZEO SG1 | 20 | 1 | 10 | 1 |
| pZEO SG2 | 300 | 300 | 3 | <1 |
| pZEO SG3 | 1 | <1 | >100 | 100 |
| pZEO SG4 | 10 | 1 | ND | ND |

Values are means of triplicate experiments.
ND: not determined

EXAMPLE 11

Murine melanoma B16 cell lines expressing the tk-VZV:sh gene simultaneously with the codA::upp gene are hypersensitive to BVaraU and FC toxicities.

By using the same protocol described above, we obtained the results depicted Table 3.

What is claimed is:

1. A eukaryotic vector containing two expression suicide gene units, a first expression suicide gene unit which sensitizes tumor cells to 5-fluorocytosine and a second expression suicide gene unit which sensitizes mammalian cells or HIV-infected cells to Azidothymidine or other pyrimidine nucleoside analogs, wherein the first and second expression suicide gene units comprise a hybrid gene coding for a single protein having both cytosine deaminase and uracil phosphoribosyl transferase activities.

2. A eukaryotic vector according to claim 1 wherein the hybrid gene is formed by the fusion of two bacterial genes or by the fusion of two fungal genes.

3. A eukaryotic vector according to claim 2 wherein the two bacterial genes are the codA gene encoding cytosine deaminase and the upp gene encoding uracil phosphoribosyl transferase from *Escherichia coli*.

4. A eukaryotic vector according to claim 2 wherein the two fungal genes are the fcy1 gene encoding cytosine deaminase and the fur1 gene encoding uracil phosphoribosyl transferase from *Saccharomyces cerevisiae*.

5. A eukaryotic vector according to any one of claims 1 to 4 wherein the second expression suicide gene unit comprises a tmk gene from *Escherichia coli* encoding thymidylate kinase.

6. A eukaryotic vector according to any one of claims 1 to 4 wherein the second expression suicide gene unit comprises a hybrid gene formed by the fusion of the tmk gene encoding thymidylate kinase and a tdk gene encoding thymidine kinase from *Escherichia coli*, said hybrid gene coding for a single protein with both thymidine kinase and thymidylate kinase activities.

7. A eukaryotic vector according to claim 6 wherein the hybrid gene comprises a further fusion with a Shble gene.

8. A eukaryotic vector according to any one of claims 1 to 4 wherein the second expression suicide gene unit comprises a hybrid gene formed by the fusion of the tmk gene from *Escherichia coli* encoding thymidylate kinase and a ndk gene from *Escherichia coli* encoding nucleoside diphosphokinase, said hybrid gene coding for a single protein with both thymidylate kinase and thymidine diphosphokinase activities.

9. A eukaryotic vector according to claim 8 wherein the hybrid gene comprises a further fusion with a Sh ble gene.

10. A eukaryotic vector according to any one of claims 1 to 4 wherein the second expression suicide gene unit comprises a tk gene from human Varicella-Zoster virus encoding thymidine kinase and thymidylate kinase activities.

11. A eukaryotic vector according to claim 10 wherein the tk gene has phleomycin resistance.

12. A eukaryotic vector according to any one of claims 1 to 4 wherein the second expression suicide gene unit comprises a tk gene from human Epstein-Barr virus encoding thymidine kinase and thymidylate kinase activities.

13. A eukaryotic vector according to claim 12 wherein the tk gene has phleomycin resistance.

14. A eukaryotic vector containing an expression suicide gene unit comprising a hybrid gene coding for a single protein having both cytosine deaminase and uracil phosphoribosyl transferase activities.

15. A eukaryotic vector according to claim 14 wherein said hybrid gene is formed by the fusion of two bacterial genes or by the fusion of two fungal genes.

16. A eukaryotic vector according to claim 14 wherein the two bacterial genes are the codA gene encoding cytosine deaminase and the upp gene encoding uracil phosphoribosyl transferase from *Escherichia coli*.

17. A eukaryotic vector according to claim 18 wherein the two fungal genes are the fcy1 gene encoding cytosine deaminase and the fur1 gene encoding uracil phosphoribosyl transferase from *Saccharomyces cerevisiae*.

18. A eukaryotic vector containing an expression suicide gene unit which sensitizes mammalian cells or HIV-infected cells to Azidothymidine or other pyrimidine nucleoside analogs, wherein said expression suicide gene unit comprises a tmk gene from *Escherichia coli* encoding thymidylate kinase.

19. A eukaryotic vector according to claim 18 wherein the pyrimidine nucleoside analog is selected from the group consisting of dideoxythymidine, trifluoromethylthymidine, ethyldeoxyuridine, bromovinyldeoxyuridine and bromovinyl-arabinouracil.

20. A eukaryotic vector according to claim 18 wherein the expression suicide gene unit comprises a hybrid gene formed by the fusion of the tmk gene encoding thymidylate kinase and a tdk gene encoding thymidine kinase from *Escherichia coli*, said hybrid gene coding for a single protein with both thymidine kinase and thymidylate kinase activities.

21. A eukaryotic vector according to claim 20 wherein the hybrid gene comprises a further fusion with a Sh ble gene.

22. A eukaryotic vector according to claim 18 wherein the second expression suicide gene unit comprises a hybrid gene formed by the fusion of the tmk gene from *Escherichia coli* encoding thymidylate kinase and a ndk gene from *Escherichia coli* encoding nucleoside diphosphokinase, said hybrid gene coding for a single protein with both thymidylate kinase and thymidine diphosphokinase activities.

23. A eukaryotic vector according to claim 22 wherein the hybrid gene comprises a further fusion with a Sh ble gene.

24. A hybrid gene coding for a single protein having both cytosine deaminase and uracil phosphoribosyl transferase activities.

25. A hybrid gene according to claim 24 wherein the hybrid gene is formed by the fusion of two bacterial genes or two fungal genes.

26. A hybrid gene according to claim 25 wherein the two bacterial genes are the codA gene encoding cytosine deaminase and the upp gene encoding uracil phosphoribosyl transferase from *Escherichia coli*.

27. A hybrid gene according to claim 25 wherein the two fungal genes are the fcy1 gene encoding cytosine deaminase and the fur1 gene encoding uracil phosphoribosyl transferase from *Saccharomyces cerevisiae*.

28. A hybrid gene formed by the fusion of a tmk gene from *Escherichia coli* encoding thymidylate kinase and a tdk gene encoding thymidine kinase from *Escherichia coli*, said hybrid gene coding for a single protein with both thymidine kinase and thymidylate kinase activities.

29. A hybrid gene according to claim 28 which comprises a further fusion with a Sh ble gene.

30. A hybrid gene formed by the fusion of a tmk gene from *Escherichia coli* encoding thymidylate kinase and a ndk gene from *Escherichia coli* encoding nucleoside diphosphokinase, said hybrid gene coding for a single protein with both thymidylate kinase and thymidine diphosphokinase activities.

31. A hybrid gene according to claim 30 which comprises a further fusion with a Sh ble gene.

32. An expression suicide gene unit comprising a tk gene from human Varicella-Zoster virus encoding thymidine kinase and thymidylate kinase activities.

33. An expression suicide gene unit according to claim 32 wherein the tk gene has phleomycin resistance.

34. An expression suicide gene unit comprising a tk gene from human Epstein-Barr virus encoding thymidine kinase and thymidylate kinase activities.

35. An expression suicide gene unit according to claim 34 wherein the tk gene has phleomycin resistance.

36. A process of sensitizing tumor cells to 5-fluorocytosine comprising transforming said tumor cells with a eukaryotic vector according to claim 1.

37. A process of sensitizing tumor cells to 5-fluorocytosine comprising transforming said tumor cells with a eukaryotic vector according to claim 14.

38. A process of sensitizing mammalian cells or HIV-infected cells to Azidothymidine or other pyrimidine nucleoside analogs comprising transforming said cells with a eukaryotic vector according to claim 18.

39. A process according to claim 38 wherein the cells are sensitized to a pyrimidine nucleoside analog selected from the group consisting of dideoxythymidine, trifluoromethylthymidine, ethyldeoxyuridine, bromovinyldeoxyuridine and bromovinyl-arabinouracil.

* * * * *